United States Patent
Subbiah et al.

(10) Patent No.: US 10,336,954 B2
(45) Date of Patent: Jul. 2, 2019

(54) COMPOSITIONS AND METHODS FOR INHIBITING FOULING IN HYDROCARBONS OR PETROCHEMICALS

(71) Applicant: General Electric Company, Schenectady, NY (US)

(72) Inventors: Alagarsamy Subbiah, Karnataka (IN); Nimeshkumar Kantilal Patel, The Woodlands, TX (US); Bryan C. Crom, The Woodlands, TX (US); Ali Fadhel, The Woodlands, TX (US); Anthony Fields, The Woodlands, TX (US); Romit Ghosh, West Bengal (IN); Andre C. G. Vanhove, Herentals (BE)

(73) Assignee: BL TECHNOLOGIES, INC., Minnetonka, MN (US)

( * ) Notice: Subject to any disclaimer, the term of this patent is extended or adjusted under 35 U.S.C. 154(b) by 225 days.

(21) Appl. No.: 14/766,306

(22) PCT Filed: Jan. 29, 2014

(86) PCT No.: PCT/US2014/013580
§ 371 (c)(1),
(2) Date: Aug. 6, 2015

(87) PCT Pub. No.: WO2014/123736
PCT Pub. Date: Aug. 14, 2014

(65) Prior Publication Data
US 2016/0010006 A1    Jan. 14, 2016

(30) Foreign Application Priority Data
Feb. 7, 2013    (IN) .............................. 353/DEL/2013

(51) Int. Cl.
*C10G 9/12*        (2006.01)
*C09K 15/06*      (2006.01)
(Continued)

(52) U.S. Cl.
CPC ........... *C10G 75/04* (2013.01); *C07D 331/02* (2013.01); *C09K 15/06* (2013.01); *C09K 15/14* (2013.01);
(Continued)

(58) Field of Classification Search
CPC ...................................................... C10G 75/04
(Continued)

(56) References Cited

U.S. PATENT DOCUMENTS 3,255,108 A    6/1966 Wiese
3,350,310 A * 10/1967 Herd .................... C10M 159/22
                                                                508/574
(Continued)

FOREIGN PATENT DOCUMENTS

EP        0 041 851 B1 B1    3/1984
GB         2444357 A          6/2008
(Continued)

OTHER PUBLICATIONS

Rudnick, Lubricants Additives, 2009, CRC Press, 2nd Edition, p. 466 (Year: 2009).*
(Continued)

*Primary Examiner* — Kevin Joyner
*Assistant Examiner* — Holly M Mull
(74) *Attorney, Agent, or Firm* — Wegman, Hessler & Vanderburg (57) ABSTRACT

Antifoulant compositions and methods are used for inhibiting fouling on structural parts of a system exposed to a fluid hydrocarbon or petrochemical stream. The antifoulant compositions may comprise at least one polyalkylene anhydride ester ("PAAE") dispersant. Other antifoulant compositions may comprise an alkylphenol sulfide ("APS").

7 Claims, 3 Drawing Sheets

(51) Int. Cl.
*C09K 15/14* (2006.01)
*C10G 75/04* (2006.01)
*C07D 331/02* (2006.01)
*C10M 141/08* (2006.01)
*C10M 129/74* (2006.01)
*C10M 129/76* (2006.01)
*C10M 129/95* (2006.01)

(52) U.S. Cl.
CPC ............. *C10G 9/12* (2013.01); *C10M 129/74* (2013.01); *C10M 129/76* (2013.01); *C10M 129/95* (2013.01); *C10M 141/08* (2013.01); C10M 2207/283 (2013.01); C10M 2207/289 (2013.01); C10M 2207/34 (2013.01); C10M 2215/28 (2013.01); C10M 2219/089 (2013.01); C10M 2223/045 (2013.01); C10M 2223/047 (2013.01); C10M 2223/065 (2013.01); C10N 2230/04 (2013.01); C10N 2230/08 (2013.01)

(58) Field of Classification Search
USPC ............................................................ 422/7
See application file for complete search history.

(56) References Cited

U.S. PATENT DOCUMENTS

| | | | |
|---|---|---|---|
| RE26,330 E | 1/1968 | Colfer | |
| 3,668,111 A | 6/1972 | Dvoracek et al. | |
| 3,708,522 A * | 1/1973 | Koft | C10L 1/1817 208/15 |
| 3,776,835 A | 12/1973 | Dvoracek | |
| 4,123,369 A | 10/1978 | Miller et al. | |
| 4,456,526 A | 6/1984 | Miller et al. | |
| 4,569,750 A * | 2/1986 | Brownawell | C10G 9/16 208/48 AA |
| 4,578,178 A | 3/1986 | Forester | |
| 4,618,539 A | 10/1986 | Jahnke et al. | |
| 4,619,756 A | 10/1986 | Dickakian | |
| 4,828,674 A | 5/1989 | Forester | |
| 4,927,519 A | 5/1990 | Forester | |
| 4,927,561 A | 5/1990 | Forester | |
| 4,936,867 A | 6/1990 | Guttierrez et al. | |
| 5,271,824 A | 12/1993 | Forester et al. | |
| 5,282,957 A | 2/1994 | Wright et al. | |
| 5,314,632 A * | 5/1994 | Papke | C10M 165/00 508/233 |
| 5,614,081 A | 3/1997 | Carey et al. | |
| 5,652,201 A | 7/1997 | Papay et al. | |
| 5,821,202 A | 10/1998 | Forester et al. | |
| 7,329,635 B2 | 2/2008 | Dickakian et al. | |
| 2009/0270531 A1 | 10/2009 | Ruhe, Jr. | |
| 2010/0170829 A1* | 7/2010 | Ng | C10G 9/00 208/48 AA |
| 2013/0008830 A1 | 1/2013 | Ng et al. | |
| 2015/0369822 A1* | 12/2015 | Strandburg | C10M 161/00 506/9 |

FOREIGN PATENT DOCUMENTS

| | | |
|---|---|---|
| WO | WO 93/06194 A1 | 4/1993 |
| WO | WO 98/33869 A1 | 8/1998 |
| WO | 2014028193 A1 | 2/2014 |

OTHER PUBLICATIONS

Ahmed, "Preparation and Evaluation of Some Lube Oil Additives Based on Polyethylene Glycol", International Journal of Polymeric Materials, vol. No. 55, pp. 761-771, Oct. 1, 2006.
International Invitation to Pay Additional Fees issued in connection with corresponding PCT Application No. PCT/US2014/013580 dated Jan. 13, 2015.
International Search Report and Written Opinion issued in connection with corresponding PCT Application No. PCT/US2014/013580 dated May 29, 2015.

* cited by examiner

COMPOSITIONS AND METHODS FOR INHIBITING FOULING IN HYDROCARBONS OR PETROCHEMICALS

FIELD OF THE INVENTION

Embodiments of the present invention relate to compositions and methods for inhibiting fouling in hydrocarbons and petrochemicals. More specifically, embodiments of the present invention relate to inhibiting fouling on structural parts exposed to a fluid hydrocarbon or petrochemical stream.

BACKGROUND OF THE INVENTION

Petroleum hydrocarbons, petrochemicals, and their feedstocks are commonly heated to temperatures ranging from 100° F. to about 1000° F. during processing. Similarly, many petroleum hydrocarbons used as heating fluids on the "hot side" of heating and heat exchange systems are also heated to such temperature ranges. When heated to elevated temperatures, petroleum hydrocarbons produce a separate phase known as fouling deposits within the petroleum hydrocarbon. As the name implies, these fouling deposits form deposits on the surfaces of processing and heating equipment, thereby fouling such surfaces. These deposits are of considerable concern in the petroleum hydrocarbon processing and heating industries.

In petroleum hydrocarbon processing, the deposits reduce the rate of heat transfer to the crude oil, and eventually, reduce throughput rates. In some cases, the fouling can even block the flow of crude oil through processing equipment and piping or clog filter screens, valves, and traps. Accordingly, fouling results in increased energy costs, increased maintenance costs for cleaning or screen replacements, and increased capital costs for the modification or replacement of refinery equipment.

The exact mechanism of fouling is not fully understood, however it appears that several different components of crude oil may contribute to fouling. Such components include asphaltenes, coke, organic polymers and organic reaction products, inorganic silicates, inorganic salts, and metal oxides or sulfides. The metal oxides or sulfides may further exacerbate fouling by accelerating the hydrocarbon oxidation rate by promoting degenerative chain branching, resulting in free radicals. The free radicals may initiate oxidation and polymerization reactions which form gum and sediments.

BRIEF DESCRIPTION OF THE INVENTION

It was surprisingly discovered that some antifoulant compositions or blends thereof produce robust antifoulant compositions that are effective at inhibiting fouling in variety of crude types or processed hydrocarbons. Specifically, these antifoulant compositions were more effective than current formulations at inhibiting fouling in some types of heavy crudes. These antifoulant compositions are also effective at inhibiting fouling tendencies in hydrocarbons and petrochemicals during high temperature processing.

Accordingly compositions and methods are disclosed for inhibiting fouling on structural parts of a system exposed to a fluid hydrocarbon or petrochemical stream. In one embodiment, a method is disclosed wherein the antifoulant composition may comprise at least one alkylphenol sulfide ("APS"). In yet another embodiment, the antifoulant composition may further comprise at least one additional antifouling component selected from a polyalkylene anhydride ester ("PAAE") dispersant, an alkyl phosphate phenate sulfide ("APPS"), a polyalkylene succinimide ("PAS"), and a polyalkylene thiophosphonic acid ester ("PETPA"). In another embodiment, the PAAE dispersant may comprise an adduct of at least one acid ester of mono- or polycarboxylic acid and an acylating reagent selected from the group consisting of fumaric acid, maleic anhydride, maleic acid, succinic anhydride, and succinic acid. In another embodiment, the ester may have a polyisobutenyl and/or a pentaerythritol moiety. In yet another embodiment, the acylating reagent may be succinic anhydride or succinic acid.

In another embodiment, the alkylphenol sulfide APS may be dodecylphenol sulfide. In yet another embodiment, the alkylphenol sulfide APS may be overbased with calcium. Likewise, the alkyl phosphate phenate sulfide APPS may be overbased with calcium.

In another method, the antifoulant composition may be added to the fluid hydrocarbon or petrochemical stream in an amount ranging from about 10 to about 100,000 ppm by volume of the fluid hydrocarbon or petrochemical stream. Alternatively, the antifoulant composition may be added to the fluid hydrocarbon or petrochemical stream in an amount ranging from about 50 to about 5,000 ppm by volume of the hydrocarbon or petrochemical stream.

In yet another method, at least one structural part is selected from hydrocarbon or petroleum storage units, heat exchangers, piping, pumps, flow meters, valves, desalters, preheat furnaces, furnaces, coker preheaters, cokers, distillation columns, fractionation columns, atmospheric columns, pipe stills, debutanizers, reactors, fluid catalytic cracking units, fluid catalytic cracking slurry settlers, hydrocracking units, steam cracking units, thermal cracking units, visbreakers, reflux units, condensers, and scrubbers.

Another method is disclosed that may comprise adding an antifoulant composition to the fluid hydrocarbon or petrochemical stream. The antifoulant composition may comprise at least one polyalkylene anhydride ester ("PAAE") dispersant. The dispersant may comprise an adduct of at least one acid ester of mono- or polycarboxylic acid and an acylating reagent selected from the group consisting of fumaric acid, maleic anhydride, maleic acid, succinic anhydride, and succinic acid. In another embodiment, the acid ester may have a polyisobutenyl and/or a pentaerythritol moiety. In another embodiment, the acylating reagent may be succinic anhydride or succinic acid. In yet another method, the dispersant may be a polyisobutenyl succinic anhydride derived ester ("PASAE") with a molecular weight, $\overline{M}w$, of about 1,000 to about 25,000 in an aromatic solvent. In another embodiment, the dispersant may be added in an amount of about 1 to about 1000 ppm by volume of the hydrocarbon or petrochemical stream.

The antifoulant composition may further comprise at least one additional antifouling component. Suitable antifouling components include, but are not limited to, an alkylphenol sulfide ("APS"), an alkyl phosphate phenate sulfide ("APPS"), a polyalkylene succinimide ("PAS"), and a polyalkylene thiophosphonic acid ester ("PETPA").

In another embodiment, at least one alkylphenol sulfide APS may be selected from the group consisting of nonylphenol sulfide and dodecylphenol sulfide. In yet another embodiment, the alkylphenol sulfide APS may be overbased with calcium. In another embodiment, the alkyl phosphate phenate sulfide APPS may be overbased with calcium.

In another embodiment, the antifoulant composition may be added to the fluid hydrocarbon or petrochemical stream in an amount ranging from about 10 to about 100,000 ppm by volume of the fluid hydrocarbon or petrochemical stream.

Alternatively, the antifoulant composition may be added to the fluid hydrocarbon or petrochemical stream in an amount ranging from about 50 to about 5,000 ppm by volume of the fluid hydrocarbon or petrochemical stream.

Antifoulant compositions for inhibiting fouling on structural parts of a system exposed to a fluid hydrocarbon or petrochemical stream are also disclosed. In one embodiment, the antifoulant composition may comprise at least one polyalkylene anhydride ester ("PAAE") dispersant. The dispersant may comprise an adduct of at least one acid ester of mono- or polycarboxylic acid and an acylating reagent selected from the group consisting of fumaric acid, maleic anhydride, maleic acid, succinic anhydride, and succinic acid. In another embodiment, the dispersant may be a polyisobutenyl succinic anhydride derived ester ("PASAE") with a molecular weight, $\overline{M}w$, of about 1,000 to about 25,000 in an aromatic solvent.

In another embodiment, the antifoulant composition may further comprise at least one additional antifouling component selected from an alkylphenol sulfide ("APS"), an alkyl phosphate phenate sulfide ("APPS"), a polyalkylene succinimide ("PAS"), and a polyalkylene thiophosphonic acid ester ("PETPA"). In another embodiment, at least one alkylphenol sulfide APS may be selected from the group consisting of nonylphenol sulfide and dodecylphenol sulfide. In another embodiment, the alkylphenol sulfide APS may be overbased with calcium. In yet another embodiment, the alkyl phosphate phenate sulfide APPS may be overbased with calcium.

Other antifoulant compositions for inhibiting fouling on structural parts of a system exposed to a fluid hydrocarbon or petrochemical stream are also disclosed comprising at least one alkyl phenol sulfide ("APS"). In yet another embodiment, the antifoulant compositions may further comprise at least one additional antifouling component selected from a polyalkylene anhydride ester ("PAAE") dispersant, an alkyl phosphate phenate sulfide ("APPS"), a polyalkylene succinimide ("PAS"), and a polyalkylene thiophosphonic acid ester ("PETPA"). In another embodiment, the dispersant may comprise an adduct of at least one acid ester of mono- or polycarboxylic acid and an acylating reagent selected from the group consisting of fumaric acid, maleic anhydride, maleic acid, succinic anhydride, and succinic acid. The dispersant may be a polyisobutenyl succinic anhydride derived ester ("PASAE") with a molecular weight, $\overline{M}w$, of about 1,000 to about 25,000 in an aromatic solvent.

In another embodiment, the alkylphenol sulfide APS may be dodecylphenol sulfide. In yet another embodiment, the alkylphenol sulfide APS may be overbased with calcium. Likewise, the phosphate phenate sulfide APPS may be overbased with calcium.

DETAILED DESCRIPTION

It was surprisingly discovered that some antifoulant compositions or blends thereof produce robust antifoulant compositions that are effective at inhibiting fouling in variety of crude types or processed hydrocarbons. Specifically, these antifoulant compositions were more effective than current formulations at inhibiting fouling in some types of heavy crudes. For example, embodiments of the antifoulant compositions are particularly effective on crudes or crude blends with an American Petroleum Institute ("API") gravity ranging from about 20 to 54 (degrees). The crudes or crude blends may comprise greater than, or equal to, about 0.1 wt % asphaltenes. These crudes may also have more than about 60 pounds of filterable solids per thousand barrels; such as 20-500 lbs., or 20-200 lbs., or 60-200 lbs. Exemplary blends for which the antifoulant compositions are particularly effective include blends of Canadian crude oils with American shale oils, sweet crudes, Bakken crude, Russian crude oil and crude oil from the United Arab Emirates. These antifoulant compositions are also effective at inhibiting fouling tendencies in hydrocarbons and petrochemicals during high temperature processing.

Without limiting the invention to one theory of operation, it is thought that the polar atoms in the dispersants and detergents of the antifouling compositions generally function to disperse and suspend the undesirable carbonaceous materials, such as asphaltene macromolecules, that form during heating of the crude oil. These polar atoms may function to chelate with the undesirable carbonaceous materials to thereby assist in the dispersion of the same in the liquid phase. Thus, the antifouling compositions inhibit or prevent the accumulation of undesirable carbonaceous materials on the internal surfaces of the equipment.

The antifoulant compositions may be added to any hydrocarbon or petrochemical system where fouling is a concern. Examples of such systems include, but are not limited to, hydrocarbon tank farms, ships, tankers, and railway cars transporting hydrocarbons, and crude oil refineries. Specific types of units found in these systems, include, but are not limited to, hydrocarbon or petroleum storage units, heat exchangers, piping, pumps, flow meters, valves, desalters, preheat furnaces, furnaces, coker preheaters, cokers, distillation columns, fractionation columns, atmospheric columns, pipe stills, debutanizers, reactors, fluid catalytic cracking units, fluid catalytic cracking slurry settlers, hydrocracking units, steam cracking units, thermal cracking units, visbreakers, reflux units, condensers, and scrubbers.

Accordingly, compositions and methods are disclosed for inhibiting fouling on structural parts of a system exposed to a fluid hydrocarbon or petrochemical stream. In one embodiment, a method is disclosed that may comprise adding an antifoulant composition to the fluid hydrocarbon or petrochemical stream. The antifoulant composition may comprise at least one polyalkylene anhydride ester ("PAAE") dispersant. The dispersant may comprise an adduct of at least one acid ester of mono- or polycarboxylic acid and an acylating reagent selected from the group consisting of fumaric acid, maleic anhydride, maleic acid, succinic anhydride, and succinic acid. In another embodiment, the acid ester may have a polyisobutenyl and/or a pentaerythritol moiety. In another embodiment, the acylating reagent may be succinic anhydride or succinic acid. In yet another method, the dispersant may be a polyisobutenyl succinic anhydride derived ester ("PASAE") with a molecular weight, $\overline{M}w$, of about 1,000 to about 25,000 in an aromatic solvent. In another embodiment, the dispersant may be added in an amount of about 1 to about 1000 ppm by volume of the hydrocarbon or petrochemical stream.

In another embodiment, a polyalkylene anhydride ester ("PAAE") dispersant, such as an alkyl succinic anhydride based material, may be used as an antifoulant composition. Alternatively, it may be used with other antifoulant compositions to improve performance. The alkyl succinic anhydride based material may be a polyisobutenyl succinic anhydride based material. The polyisobutenyl succinic anhydride-based material does not have nitrogen, sulfur or metals, making it more environmentally friendly than many other dispersants, in addition to being harmless to the processing of hydrocarbons and petrochemicals. The polyisobutenyl succinic anhydride-based material is not just useful in upstream applications, such as oil fields and transportation vessels, it may be used in downstream applications, for example in a refinery in the preheat train or in hydrotreaters. In addition, this material has special properties that will work conjunctively with demulsifying compositions to better resolve emulsions in the desalting processes.

Asphaltenes in the crude oil are believed to have hydrophilic functionalities which may result in a colloidal aggregation or flocculation of the asphaltenes due to the insolubility in a given composition of the hydrocarbon or petrochemical mixture, resulting in adsorption at the interface of the aqueous phase and oil phase in a desalter, or at other metallic surfaces of processing equipment. The antifoulant compositions are believed to adsorb onto the asphaltenes and decrease the colloidal aggregation or flocculation and deposition of the asphaltenes at the oil-water interface and surfaces of processing equipment to both accelerate emulsion resolution and mitigate fouling.

The polyalkylene anhydride ester ("PAAE") dispersant may be a treated ester that is a mono- or polycarboxylic acid ester that is further treated with an acylating reagent. The mono- or polycarboxylic acid ester may have at least one moiety that is a polyol as shown in any of the following three formulas:

where $R^1$, $R^2$, $R^3$, and $R^4$ are the same or different and are selected from the group consisting of H, an alkyl, and —CH(OH)($R^5$); wherein $R^5$ is H or $C_1$ to $C_{10}$ alkyl; and wherein X and Y are the same or different and are H or $C_1$ to $C_{10}$ alkyl, with the proviso that at least one of $R^1$, $R^2$, $R^3$, and $R^4$ is the —CH(OH)($R^5$) moiety. Suitable alkyls may be polyalkenes, including interpolymers of various alkenes, and may include, but are not limited to, ethylene, propene, isoprene, 1-butene, 2-butene, isobutene, 3-pentene, 1-hexene, 1-octene, 4-oxtene, 2-methyl-1-heptene, 3-cyclohexyl-1-butene, 2-methyl-5-propyl-1-hexene, styrene, butadiene, and piperylene. The —CH(OH)($R^5$) moiety may be mono or polyhydric alcohols, more particularly polyhydric, such as glycerol, erythritol, pentaerythritol, mannitol, and sorbitol.

The acylating reagent may be aliphatic mono- or polycarbocylic acids, anhydrides, or halides. Suitable acylating reagents may include, but are not limited to, fumaric acid, maleic anhydride, maleic acid, succinic anhydride, and succinic acid.

In an embodiment, the acid ester has a polyisobutenyl and pentaerythritol moiety and is treated with succinic anhydride or succinic acid such that the dispersant is a polyisobutenyl succinic anhydride ester ("PiBS ester") with a polyol moiety as in the following formula:

wherein R is a polyisobutenyl moiety.

Accordingly, in another embodiment, an alkyl succinic anhydride based material, such as a polyisobutenyl succinic anhydride based material may be used as the dispersant. The polyisobutenyl succinic anhydride based material may be a polyisobutenyl succinic anhydride derived ester with a molecular weight, $\overline{M}w$, of about 1,000 to about 25,000 in an aromatic solvent. The % actives may range from about 10-50% and the solvent may be aromatic naphtha.

The antifoulant composition may further comprise at least one additional antifouling component. Suitable antifouling components include, but are not limited to, an alkylphenol sulfide ("APS"), an alkyl phosphate phenate sulfide ("APPS"), a polyalkylene succinimide ("PAS"), and a polyalkylene thiophosphonic acid ester ("PETPA"). The ratio by weight of an amount of the first polyalkylene anhydride ester ("PAAE") dispersant relative to the additional antifouling component or components may be 1:9 to 9:1.

As used herein, an APS is an alkylphenol sulfide salt highly overbased with an alkaline earth metal, such as calcium (Ca), manganese (Mg), or barium (Ba), to neutralize the salt. The alkaline earth metal may be the oxides or hydroxides of alkaline earth metals such as $Ca(OH)_2$, CaO, MgO, $Mg(OH)_2$, etc. Accordingly, in one embodiment, the alkylphenol sulfide APS may be overbased with calcium.

A suitable APS may have the general formula:

where $R^6$ is a $C_5$ to $C_{24}$ alkyl, x is an integer from 1 to 4, y is an integer from 0 to 3, and z is an integer from 1 to 5. Accordingly, in another embodiment, at least one alkylphenol sulfide APS may be selected from the group consisting of nonylphenol sulfide and dodecylphenol sulfide.

A portion of the APS described above may be esterified with phosphoric acid to produce an alkyl phosphate phenate sulfide APPS wherein about 20-40% of the phenol hydroxy groups have been phosphonated. In yet another embodiment, the alkyl phosphate phenate sulfide APPS may be overbased with calcium.

The polyalkylene succinimide ("PAS") may be the reaction product of an alkyl succinic acid or anhydride and a polyalkylene polyamine. A suitable PAS includes polyisobutenyl succinimide that is a reaction product of ethylenediamine or diethylenetriamine with a polyisobutenyl succinic anhydride. The polyalkylene thiophosphonic acid ester PETPA may be the reaction product of alkenyl polymers with $P_2S_5$. A suitable PETPA includes the reaction product that is a pentaerythritol ester of polyisobutenylthiophosphonic acid wherein the polisobutenyl moiety has an average molecular weight of about 1300.

In another embodiment, the antifoulant composition may be added to the fluid hydrocarbon or petrochemical stream in an amount ranging from about 10 to about 100,000 ppm by volume of the fluid hydrocarbon or petrochemical stream. Alternatively, the antifoulant composition may be added to the fluid hydrocarbon or petrochemical stream in an amount ranging from about 50 to about 5,000 ppm by volume of the fluid hydrocarbon or petrochemical stream.

Another method is disclosed wherein the antifoulant composition may comprise at least one alkylphenol sulfide ("APS"). In yet another embodiment, the antifoulant composition may further comprise at least one additional antifouling component selected from a polyalkylene anhydride ester ("PAAE") dispersant, an alkyl phosphate phenate sulfide ("APPS"), a polyalkylene succinimide ("PAS"), and a polyalkylene thiophosphonic acid ester ("PETPA"). In another embodiment, the PAAE dispersant may comprise an adduct of at least one acid ester of mono- or polycarboxylic acid and an acylating reagent selected from the group consisting of fumaric acid, maleic anhydride, maleic acid, succinic anhydride, and succinic acid. In another embodiment, the ester may have a polyisobutenyl and/or a pentaerythritol moiety. In yet another embodiment, the acylating reagent may be succinic anhydride or succinic acid. In another embodiment, the alkylphenol sulfide APS may be dodecylphenol sulfide. The ratio by weight of an amount of the first alkylphenol sulfide ("APS") relative to the additional antifouling component or components may be 1:9 to 9:1.

In another method, the antifoulant composition may be added to the fluid hydrocarbon or petrochemical stream in an amount ranging from about 10 to about 100,000 ppm by volume of the fluid hydrocarbon or petrochemical stream. Alternatively, the antifoulant composition may be added to the fluid hydrocarbon or petrochemical stream in an amount ranging from about 50 to about 5,000 ppm by volume of the hydrocarbon or petrochemical stream.

Antifoulant compositions for inhibiting fouling on structural parts of a system exposed to a fluid hydrocarbon or petrochemical stream are also disclosed. In one embodiment, the antifoulant composition may comprise at least one polyalkylene anhydride ester ("PAAE") dispersant. The dispersant may comprise an adduct of at least one acid ester of mono- or polycarboxylic acid and an acylating reagent selected from the group consisting of fumaric acid, maleic anhydride, maleic acid, succinic anhydride, and succinic acid. In another embodiment, the dispersant may be a polyisobutenyl succinic anhydride derived ester ("PASAE") with a molecular weight, $\overline{M}w$, of about 1,000 to about 25,000 in an aromatic solvent.

In another embodiment, the antifoulant composition may further comprise at least one additional antifouling component selected from an alkylphenol sulfide ("APS"), an alkyl phosphate phenate sulfide ("APPS"), a polyalkylene succinimide ("PAS"), and a polyalkylene thiophosphonic acid ester ("PETPA"). In another embodiment, at least one alkylphenol sulfide APS may be selected from the group consisting of nonylphenol sulfide and dodecylphenol sulfide. In another embodiment, the alkylphenol sulfide APS may be overbased with calcium. In yet another embodiment, the alkyl phosphate phenate sulfide APPS may be overbased with calcium.

Other antifoulant compositions for inhibiting fouling on structural parts of a system exposed to a fluid hydrocarbon or petrochemical stream are also disclosed comprising at least one alkyl phenol sulfide ("APS"). In yet another embodiment, the antifoulant compositions may further comprise at least one additional antifouling component selected from a polyalkylene anhydride ester ("PAAE") dispersant, an alkyl phosphate phenate sulfide ("APPS"), a polyalkylene succinimide ("PAS"), and a polyalkylene thiophosphonic acid ester ("PETPA"). In another embodiment, the dispersant may comprise an adduct of at least one acid ester of mono- or polycarboxylic acid and an acylating reagent selected from the group consisting of fumaric acid, maleic anhydride, maleic acid, succinic anhydride, and succinic acid. The dispersant may be a polyisobutenyl succinic anhydride derived ester ("PASAE") with a molecular weight, $\overline{M}w$, of about 1,000 to about 25,000 in an aromatic solvent.

In another embodiment, the alkylphenol sulfide APS may be dodecylphenol sulfide. In yet another embodiment, the alkylphenol sulfide APS may be overbased with calcium. Likewise, the phosphate phenate sulfide APPS may be overbased with calcium.

EXAMPLES

HLPS Antifoulant Test

A Hot Liquid Process Simulator ("HLPS") was used to compare the antifouling efficacy of overbased calcium dodecylphenol sulfides ("DDPS") and DDPS blends with currently used antifoulant compositions.

The HLPS is an annular heat exchanger with a steel tube in the center that is heated to a constant temperature. Oil samples with various treatment compositions are passed once through the annulus. As fouling deposits build up on the heated tube surface, the deposits act as an insulator, resulting in a temperature drop in the oil sample at the annulus outlet. The overall heat-transfer coefficient, U, is calculated every 2 minutes during the test by measuring the temperatures of the oil sample at the inlet and outlet of the annulus. The U coefficient is then used to calculate the area under the various heat-transfer curves of the treated oil samples. These areas are then compared with the area under the heat-transfer curve for a control, or blank, wherein no antifoulant treatment is added. The percent reduction in fouling is determined by comparing the calculated area under the heat-transfer curve for a control, or blank, ($A_{Control}$) with the calculated area under the heat-transfer curve of the treated oil samples ($A_{Treat}$) as in equation 1.

$$\% \text{ Reduction} = \frac{(A_{Treat} - A_{Control})}{A_{Control}} \times 100 \quad (1)$$

Figure 1:
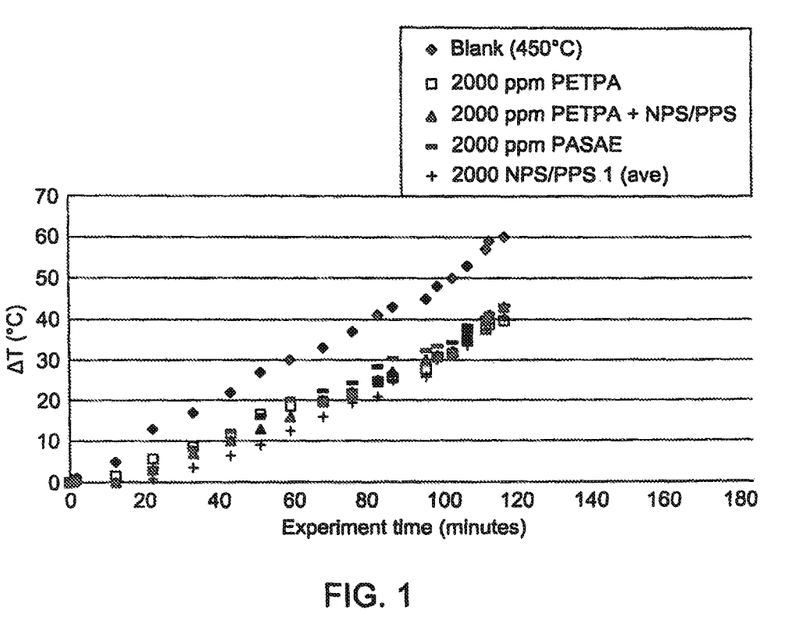
FIG. 1 shows Hot Liquid Process Simulator ("HLPS") HLPS curves of the differences in inlet and outlet temperatures of various treatments in flashed crude from the United States.

FIG. 1 shows the curves of the differences in inlet and outlet temperatures of various treatments in flashed crude from the United States. The inner steel tube of the HLPS was maintained at 450° C. The exemplary treatment composition included a polyalkylene anhydride ester dispersant; in this case, a polyisobutenyl succinic anhydride derived ester ("PASAE"). The comparative treatment compositions included blends of calcium overbased nonylphenol sulfides and overbased calcium alkyl phosphate phenate sulfides ("NPS/PPS 1"), a polyalkylenemethiophosphonic acid ester ("PETPA"), and a blend thereof ("PETPA+NPS/PPS"). The data for NPS/PPS 1 is an average of two HLPS test results.

Figure 2:
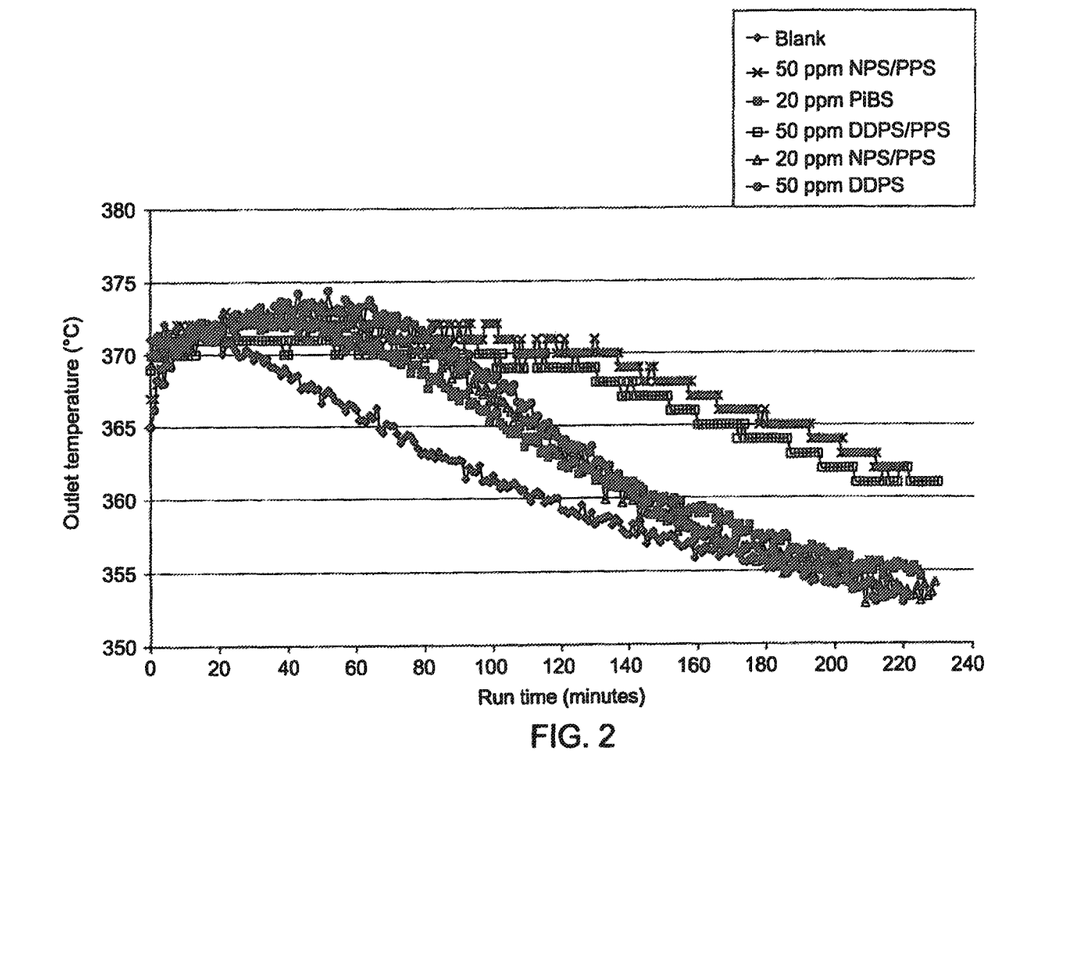
FIG. 2 shows HLPS outlet temperature curves of various treatments in residual oil from the United Arab Emirates.

FIG. 2 shows the curves of the outlet temperature of various treatments in residual oil from the United Arab Emirates. The inner steel tube of the HLPS was maintained at 550° C. The exemplary treatment compositions included overbased calcium dodecylphenol sulfides ("DDPS") and blends of DDPS and overbased calcium alkyl phosphate phenate sulfides ("DDPS/PPS"). The comparative treatment compositions included polyisobutylene succinimide ("PiBS") and a blend of calcium overbased nonylphenol sulfides and overbased calcium alkyl phosphate phenate sulfides ("NPS/PPS"). The percent reduction in fouling ("% Reduction") in the treated residual oil samples was 2.7% for the PiBS-treated oil, 15% for the oil treated with 20 ppm NPS/PPS, 28.8% for the oil treated with 50 ppm NPS/PPS, 25.2% for the DDPS-treated residual oil, and 26.3% for the DDPS/PPS-treated residual oil.

Figure 3:
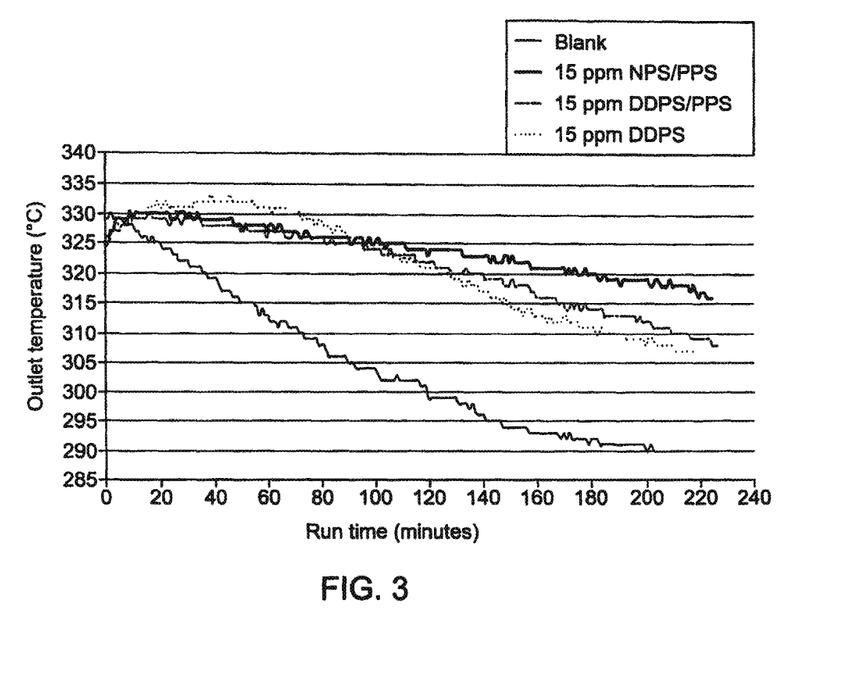
FIG. 3 shows HLPS outlet temperature curves of various treatments in gas oil from the Russian Federation.

FIG. 3 shows the curves of the outlet temperature of various treatments in gas oil from the Russian Federation. The inner steel tube of the HLPS was maintained at 525° C. The exemplary treatment compositions included overbased calcium dodecylphenol sulfides ("DDPS") and blends of DDPS and overbased calcium alkyl phosphate sulfides ("DDPS/PPS"). The comparative treatment composition was a blend of calcium overbased nonylphenol sulfides and overbased calcium alkyl phosphate phenate sulfides ("NPS/PPS"). The percent reduction in fouling ("% Reduction") in the treated gas oil samples was 50.1% for NPS/PPS-treated gas oil, 55.3% for the DDPS-treated gas oil, and 59.4% for the DDPS/PPS-treated gas oil.

Turbiscan® Test

As the detergents and dispersants are thought to disperse and suspend the undesirable carbonaceous materials in the liquid hydrocarbon phase, the effectiveness of various treatments may be evaluated by evaluating the stability, or in contrast, the separability of the dispersions created by the various treatments. A Turbiscan® dispersion stability analyzer measures the separability of a given dispersion by measuring light backscattering and transmission along the height of the sample with respect to time. Accordingly, the analyzer detects particle migration and changes in particle size. Both particle migration and an increase in particle size may indicate separation of the solid and liquid phases in the dispersion. Thus, samples with a low separability number are highly stable dispersions that are less likely to result in the accumulation of fouling deposits in the interior surfaces of equipment.

The Turbiscan® results of various treatments on different crude sources are shown in Tables 1 through 4 below. Table 1 shows the separability numbers of various treatment compositions on asphaltenic crude ("Batch 1") from U.S. location A. The comparative treatment compositions are either a polyalkylenemethiophosphonic acid ester ("PETPA"), a polyisobutylene succinimide ("PiBS"), or blends of calcium overbased nonylphenol sulfides and overbased calcium alkyl phosphate phenate sulfides ("NPS/PPS"). All the exemplary treatment compositions comprise a calcium overbased dodecylphenol sulfide salt ("DDPS"). In addition to DDPS, the exemplary compositions may further comprise known antifoulant compositions such as NPS/PPS, PETPA, PiBS, or combinations thereof.

TABLE 1

U.S. Location A; Batch 1

| | Treatment (ppm) | | | | Performance Separability |
|---|---|---|---|---|---|
| | NPS/PPS | PETPA | PiBS | DDPS | Number |
| Exemplary | | | 100 | 400 | 3.9 |
| Exemplary | | 250 | | 250 | 4 |
| Comparative | 500 | | | | 4.4 |
| Exemplary | | | | 500 | 4.4 |
| Comparative | | 500 | | | 6.1 |
| Exemplary | | 250 | | 250 | 7 |
| Exemplary | | 150 | 150 | 200 | 9.8 |
| Exemplary | | | 400 | 100 | 10.6 |
| Comparative | | | 500 | | 12.8 |
| Blank | | | | | 12.7 |

Table 2 shows the separability numbers of various treatment compositions on a second batch of asphaltenic crude ("Batch 2") from U.S. location A. The comparative treatment compositions are either polyalkylenemethiophosphonic acid ester ("PETPA"), blends of calcium overbased nonylphenol sulfides and overbased calcium alkyl phosphate phenate sulfides ("NPS/PPS"), or blends of PETPA and NPS/PPS. All the exemplary treatment compositions comprise a calcium overbased dodecylphenol sulfide salt ("DDPS"). In addition to DDPS, the exemplary compositions may further comprise known antifoulant compositions such as NPS/PPS, PETPA, PiBS, or combinations thereof.

TABLE 2

U.S. Location A; Batch 2

| | Treatment (ppm) | | | Performance Separability |
|---|---|---|---|---|
| | NPS/PPS | PETPA | DPPS | Number |
| Exemplary | 100 | | 100 | 0.2 |
| Exemplary | | 100 | 100 | 2.6 |
| Exemplary | | | 200 | 2.6 |
| Comparative | 100 | 100 | | 4.2 |
| Exemplary | | 50 | 150 | 6 |
| Comparative | 200 | | | 7.3 |
| Exemplary | | 150 | 50 | 8.5 |
| Comparative | | 200 | | 11.3 |
| Blank | | | | 12.8 ± 0.7 |

Table 3 shows the separability numbers of various treatment compositions on crude from U.S. location B. The comparative treatment compositions are either polyalkylenemethiophosphonic acid ester ("PETPA"), blends of calcium overbased nonylphenol sulfides and overbased calcium alkyl phosphate phenate sulfides ("NPS/PPS"), or blends of PETPA and NPS/PPS. All the exemplary treatment compositions comprise a calcium overbased dodecylphenol sulfide salt ("DDPS"). In addition to DDPS, the exemplary compositions may further comprise known antifoulant compositions such as NPS/PPS, PETPA, PiBS, or combinations thereof.

TABLE 3

| U.S. Location B | | | |
|---|---|---|---|
| Treatment (ppm) | | | Performance Separability |
| NPS/PPS | PETPA | DPPS | Number |
| Exemplary 100 | | 100 | 0.3 |
| Exemplary | | 200 | 0.8 |
| Exemplary | 50 | 150 | 2.6 |
| Exemplary | 100 | 100 | 3.8 |
| Comparative 200 | | | 8.5 |
| Exemplary | 150 | 50 | 9.9 |
| Comparative 100 | 100 | | 13.8 |
| Comparative | 200 | | 11.8 ± 0.3 |
| Blank | | | 13.1 ± 0.6 |

Table 4 shows the separability numbers of various treatment compositions on crude from U.S. location C. The comparative treatment compositions are either a polyalkylenemethiophosphonic acid ester ("PETPA"), a polyisobutylene succinimide ("PiBS"), or blends of calcium overbased nonylphenol sulfides and overbased calcium alkyl phosphate phenate sulfides ("NPS/PPS"). All the exemplary treatment compositions comprise a calcium overbased dodecylphenol sulfide salt ("DDPS") or a polyisobutenyl succinic anhydride derived ester ("PASAE"). Exemplary treatment compositions may comprise both DDPS and PASAE and/or may further comprise known antifoulant compositions such as NPS/PPS, PETPA, PiBS, or combinations thereof.

TABLE 4

| U.S. Location C | | | | | |
|---|---|---|---|---|---|
| Treatment (ppm) | | | | | Performance |
| NPS/PPS | PETPA | PiBS | DDPS | PASAE | Separability Number |
| Exemplary | | | | 1000 | 1.9 |
| Exemplary | 200 | | 800 | | 3.9 |
| Exemplary | 500 | | 500 | | 4.0 |
| Comparative 1000 | | | | | 4.4 |
| Exemplary | | | 1000 | | 4.4 |
| Comparative | 1000 | | | | 6.1 |
| Exemplary | | 500 | 500 | | 7.0 |
| Exemplary | 300 | 300 | 400 | | 9.8 |
| Exemplary | | 800 | 200 | | 10.6 |
| Comparative | | 1000 | | | 12.7 |
| Blank | | | | | 12.7 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An antifoulant composition for inhibiting fouling on structural parts of a system exposed to a fluid hydrocarbon or petrochemical stream, said antifoulant composition comprising (1) at least one polyalkylene anhydride ester ("PAAE") dispersant, wherein said dispersant is a polyisobutenyl succinic anhydride derived ester ("PASAE") with a molecular weight, Mw, of about 1,000 to about 25,000, wherein said polyisobutenyl succinic anhydride ester ("PASAE") includes a polyol moiety, wherein said polyol moiety is represented by the formula (I)

wherein R is a polyisobutenyl moiety, said dispersant providing a stable dispersion when mixed with said fluid hydrocarbon or petrochemical stream, wherein said fluid hydrocarbon or petrochemical stream comprises heavy crudes or crude blends,
wherein said at least one structural part is selected from the group consisting of hydrocarbon or petroleum storage units, heat exchangers, piping, pumps, flow meters, valves, desalters, preheat furnaces, furnaces, coker preheaters, cokers, distillation columns, fractionation columns, atmospheric columns, pipe stills, debutanizers, reactors, fluid catalytic cracking units, fluid catalytic cracking slurry settlers, hydrocracking units, steam cracking units, thermal cracking units, visbreakers, reflux units, condensers, and scrubbers.

2. The antifoulant composition of claim 1, wherein said antifoulant composition further comprises at least one additional antifouling component selected from components (2), (3), (4), and (5) wherein:
component (2) is an alkylphenol sulfide ("APS");
component (3) is an alkyl phosphate phenate sulfide ("APPS");
component (4) is a polyalkylene succinimide ("PAS"); and
component (5) is a polyalkylene thiophosphonic acid ester ("PETPA").

3. The antifoulant composition of claim 2, wherein said alkylphenol sulfide APS is present and is selected from the group consisting of nonylphenol sulfide and dodecylphenol sulfide.

4. The antifoulant composition of claim 3, wherein said nonylphenol sulfide and said dodecylphenol sulfide are both present and are each overbased with calcium.

5. The antifoulant composition of claim 1 wherein 100 ppm of said dispersant, based upon 1 million parts of said fluid hydrocarbon or petrochemical stream provides said stable dispersion.

6. The antifoulant composition of claim 1, wherein the fluid hydrocarbon or petrochemical stream is present at a temperature range of about 250° C. to about 550° C.

7. An antifoulant composition for inhibiting fouling on structural parts of a system exposed to a fluid hydrocarbon or petrochemical stream, said antifoulant composition comprising
(1) at least one polyalkylene anhydride ester ("PAAE") dispersant, wherein said dispersant is a polyisobutenyl succinic anhydride derived ester ("PASAE") with a molecular weight, Mw, of about 1,000 to about 25,000, wherein said polyisobutenyl succinic anhydride ester ("PASAE") includes a polyol moiety, wherein said polyol moiety is represented by the formula wherein R is a polyisobutenyl moiety, said dispersant providing a stable dispersion when mixed with said fluid hydrocarbon or petrochemical stream, wherein said fluid hydrocarbon or petrochemical stream comprises heavy crudes or crude blends, wherein the fluid hydrocarbon or petrochemical stream is present at a temperature range of about 250° C. to about 550° C.; and at least one additional antifouling component selected from components (2), (3), (4), and (5) wherein:
component (2) is an alkylphenol sulfide ("APS");
component (3) is an alkyl phosphate phenate sulfide ("APPS");
component (4) is a polyalkylene succinimide ("PAS"); and
component (5) is a polyalkylene thiophosphonic acid ester ("PETPA").

* * * * *